United States Patent
Lowe

(10) Patent No.: US 9,310,357 B2
(45) Date of Patent: Apr. 12, 2016

(54) DETECTION OF CHEMICAL AND BIOLOGICAL AGENTS USING OLIGONUCLEOTIDE APTAMERS

(71) Applicant: SRC, Inc., North Syracuse, NY (US)

(72) Inventor: Adam J. Lowe, Syracuse, NY (US)

(73) Assignee: SRC, INC., North Syracuse, NY (US)

( * ) Notice: Subject to any disclaimer, the term of this patent is extended or adjusted under 35 U.S.C. 154(b) by 620 days.

(21) Appl. No.: 13/630,189

(22) Filed: Sep. 28, 2012

(65) Prior Publication Data

US 2015/0005181 A1    Jan. 1, 2015

(51) Int. Cl.
*C12Q 1/68* (2006.01)
*G01N 33/53* (2006.01)
*C12N 15/115* (2010.01)

(52) U.S. Cl.
CPC .......... *G01N 33/5308* (2013.01); *C12N 15/115* (2013.01)

(58) Field of Classification Search
None
See application file for complete search history.

(56) References Cited

U.S. PATENT DOCUMENTS

| | | | |
|---|---|---|---|
| 6,569,630 B1 | 5/2003 | Vivekananda et al. | |
| 7,029,852 B2 | 4/2006 | Liebholz et al. | |
| 7,291,496 B2 | 11/2007 | Holm-Kennedy | |
| 7,316,899 B2 | 1/2008 | McDevitt et al. | |
| 7,736,909 B2 | 6/2010 | Kodadek | |
| 7,811,809 B2 | 10/2010 | Heyduk et al. | |
| 2004/0023266 A1 | 2/2004 | Vivekananda et al. | |
| 2008/0156646 A1 | 7/2008 | Wu et al. | |
| 2008/0176263 A1 | 7/2008 | Schultz et al. | |
| 2010/0075340 A1 | 3/2010 | Javanmard et al. | |
| 2010/0227382 A1 | 9/2010 | Lieber et al. | |
| 2010/0240544 A1 | 9/2010 | Liu et al. | |
| 2011/0136099 A1 | 6/2011 | Schneider et al. | |
| 2013/0157279 A1* | 6/2013 | Takoh | 435/6.12 |

FOREIGN PATENT DOCUMENTS

| | | | |
|---|---|---|---|
| WO | WO 2006086669 A2 * | 8/2006 | |
| WO | 2010093223 A2 | 8/2010 | |
| WO | WO 2012029224 A1 * | 3/2012 | |

OTHER PUBLICATIONS

Endoh et al (2007) "Construction of Intramolecular Luciferase Complementation Probe for Detecting Specific RNA" Bioconjugate Chem 18(3):956-961.*

(Continued)

*Primary Examiner* — Tracy Vivlemore
*Assistant Examiner* — Karen S Weiler
(74) *Attorney, Agent, or Firm* — George McGuire; Blaine Bettinger; Bond Schoeneck & King, PLLC

(57) ABSTRACT

Methods and systems for detecting chemical and biological agents using oligonucleotide aptamers. A sensor includes a detection complex between an aptamer that has a binding domain for the chemical or biological agent, and a first oligonucleotide with a sequence complementary to a region of the aptamer. In the absence of the agent, the aptamer and the first oligonucleotide form an intermediate combination. In the presence of the agent, the intermediate combination dissociates. The sensor further includes a second oligonucleotide with a sequence that interacts with a region of the first oligonucleotide to form a duplex structure only when the first oligonucleotide is dissociated from the aptamer. When the duplex structure is formed, it can interact with a reporter molecule which in turn initiates a signal reporting detection of the chemical or biological agent.

14 Claims, 6 Drawing Sheets

(56) References Cited

OTHER PUBLICATIONS

Deng et al., "Highly Effective Colorimetric and Visual Detection of Nucleic Acids Using an Asymmetrically Split Peroxidase DNAzyme", J. Am. Chem. Soc., 2008, 130 (39), pp. 13095-13102.

Lin et al., "Signal-on electrochemiluminescence biosensor for thrombin based on target-induced conjunction of split aptamer fragments", Chem. Commun., 2010, 46, pp. 5563-5565.

Mehta et al., "The Use of Phages and Aptamers as Alternatives to Antibodies in Medical and Food Diagnostics" Biomedical Engineering, Trends, Research and Technologies, http://www.intechopen.com/source/pdfs/12836/InTechThe_use_of_phages_and_aptamers_as_alternatives_to_antibodies_in_medical_and_food_diagnostics.pdf.

Zuo et al., "High Specificity, Electrochemical Sandwich Assays Based on Single Aptamer Sequences and Suitable for the Direct Detection of Small-Molecule Targets in Blood and Other Complex Matrices" J. Am. Chem. Soc., 2009, 131 (20), pp. 6944-6945.

\* cited by examiner

DETECTION OF CHEMICAL AND BIOLOGICAL AGENTS USING OLIGONUCLEOTIDE APTAMERS

BACKGROUND OF THE INVENTION

1. Field of the Invention

The present invention relates to detection of chemical and biological agents and, more specifically, to detection of chemical and biological agents using oligonucleotide aptamers.

2. Description of the Related Art

There is an increasing demand for assays for the detection and quantitative identification of chemical and biological hazards across a broad range of disciplines, including food safety, homeland security, and medical diagnostics. While there is existing technology for the detection and quantitative identification of chemical and biological hazards, these sensors are generally large, bulky, and/or slow sensor systems that require considerable time and effort to utilize or to move from one location to another. Accordingly, there is a continued need for fast, efficient, and portable sensor systems for chemical and biological hazard detection.

Aptamers are single-stranded oligonucleic acid or peptide molecules that bind to a specific target molecule. The target molecule can be, for example, a protein, nucleic acid, cell, or tissue, among many others. While some aptamers are naturally occurring, most are designed for a specific target. Due to the high affinity and specificity for their target(s) of interest, aptamers are increasingly used as diagnostic reagents. Accordingly, aptamers are a potential component of sensors for the detection and quantitative identification of chemical and biological hazards.

BRIEF SUMMARY OF THE INVENTION

It is therefore a principal object and advantage of the present invention to provide a method, device, and/or system for the detection of chemical and biological hazards.

It is another object and advantage of the present invention to provide a method, device, and/or system that utilizes aptamer technology to detect chemical and biological hazards.

It is yet another object and advantage of the present invention to provide a wearable, aptamer-based sensor for the detection of chemical and biological hazards.

Other objects and advantages of the present invention will in part be obvious, and in part appear hereinafter.

Embodiments include systems and methods for detecting chemical and biological agents using oligonucleotide aptamers. A sensor for detecting the chemical and/or biological target comprises: (i) a detection complex comprising (a) an aptamer having a binding domain for the target, and (b) a first oligonucleotide having a sequence complementary to a region of the aptamer, where in the absence of the target the aptamer and the complementary region of the first oligonucleotide form an intermediate combination, and where in the presence of the target the intermediate combination dissociates; (ii) a second oligonucleotide having a sequence that interacts with a region of the first oligonucleotide to form a duplex structure only when the first oligonucleotide is dissociated from the intermediate combination; and (iii) a reporter molecule having a region that interacts with the duplex structure to form a reporter complex, where the reporter complex initiates a reporter signal. The A further embodiment comprises a sensor array for detecting a plurality of chemical and biological agents. The sensor array comprises a plurality of detection sensors, each sensor comprising: (i) a detection complex comprising: (a) an aptamer having a binding domain for the chemical or biological agent, and (b) a first oligonucleotide having a sequence complementary to a region of the aptamer, where in the absence of the target the aptamer and the complementary region of the first oligonucleotide form an intermediate combination, and where in the presence of the target the intermediate combination dissociates; (ii) a second oligonucleotide comprising a metal nanoparticle and having a sequence that interacts with a region of the first oligonucleotide to form a duplex structure only when the first oligonucleotide is dissociated from the intermediate combination; and (iii) a reporter molecule having a region that interacts with the duplex structure to form a reporter complex, where the reporter complex initiates a reporter signal.

Yet another embodiment comprises a method of detecting a chemical and/or biological target. The method comprises the steps of: (i) contacting a sample with a sensor comprising a detection complex, the detection complex comprising: (a) an aptamer having a binding domain for the target, and (b) a first oligonucleotide having a sequence complementary to a region of the aptamer, where in the absence of the target the aptamer and the complementary region of the first oligonucleotide form an intermediate combination, and where in the presence of the target the intermediate combination dissociates; (ii) forming a duplex structure between the dissociated first oligonucleotide and a second oligonucleotide, the second oligonucleotide comprising a nanoparticle and having a sequence that interacts with a region of the first oligonucleotide only when the first oligonucleotide is dissociated from the intermediate combination; (iii) forming a reporter complex between the duplex structure and a reporter molecule; and (iv) generating a reporter signal by the reporter complex.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
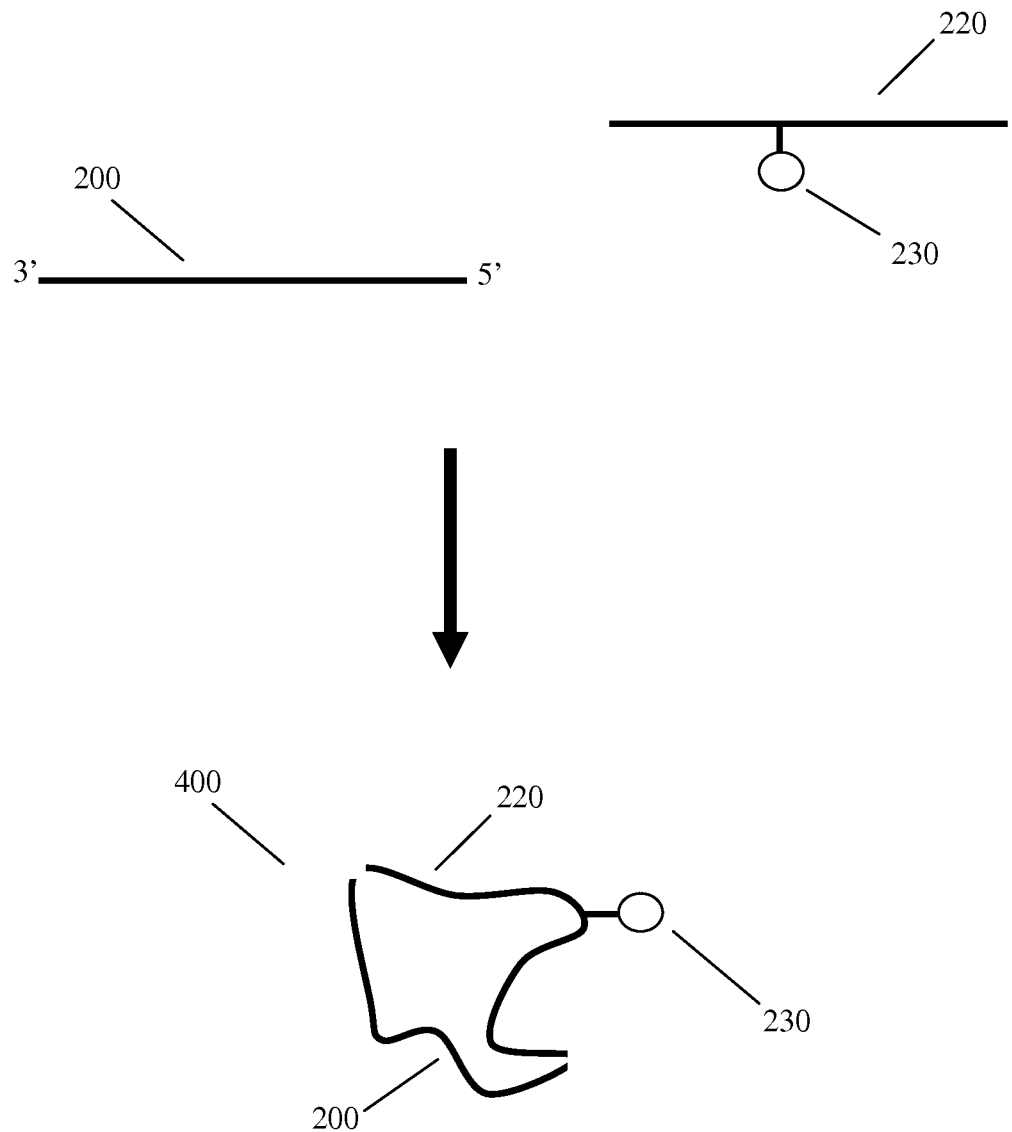
Figure 5:
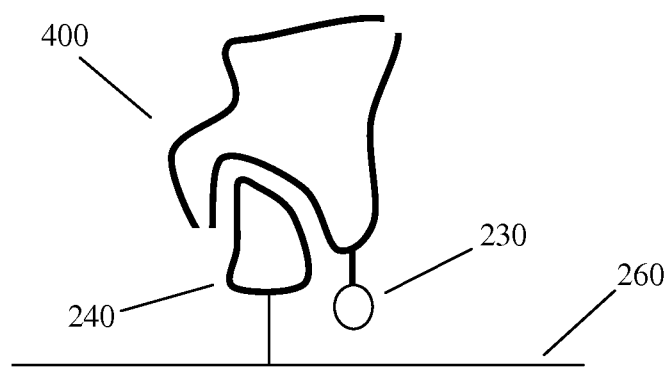
Figure 6:
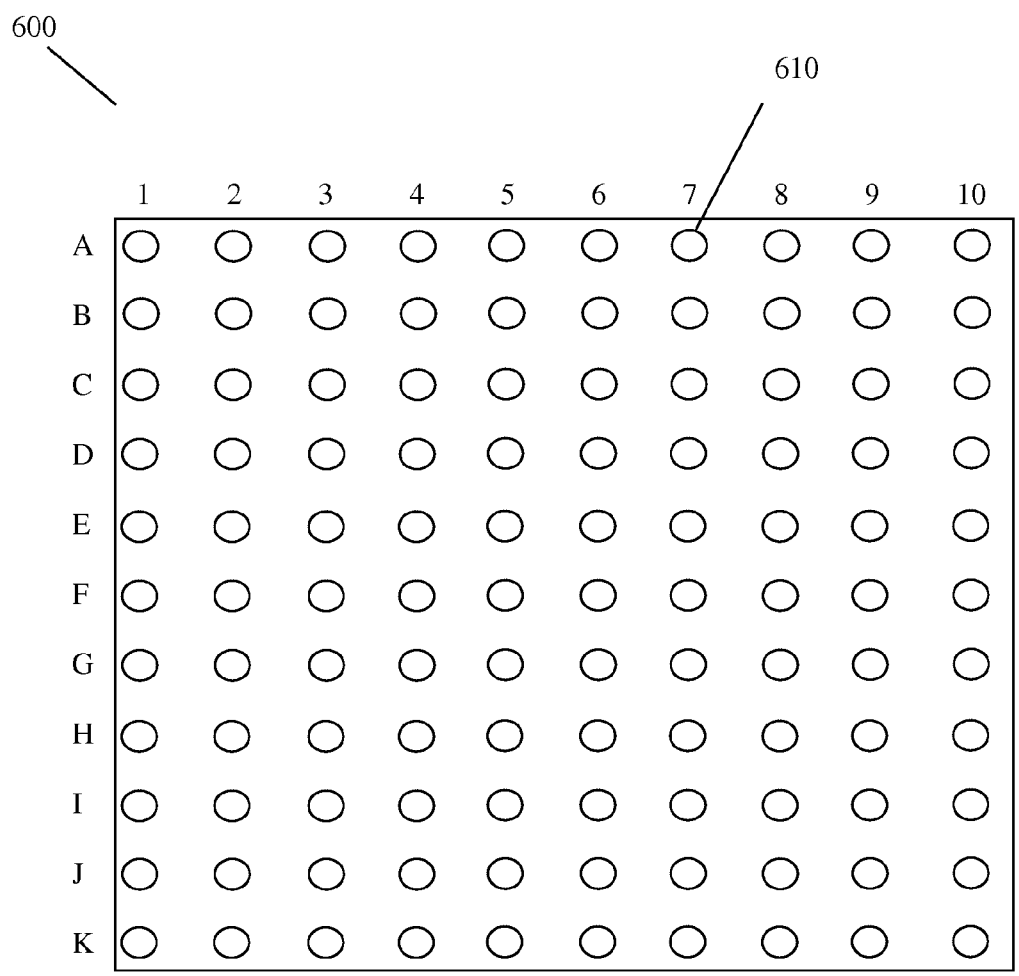

FIG. 4 is a schematic representation of a system for detecting the presence of a chemical or biological agent using an aptamer in accordance with an embodiment of the present invention; and FIG. 5 is a schematic representation of a system for detecting the presence of a chemical or biological agent using an aptamer in accordance with an embodiment of the present invention; and FIG. 6 is a schematic representation of an array for detecting the presence of a chemical or biological agent using an aptamer in accordance with an embodiment of the present invention.

DETAILED DESCRIPTION OF THE INVENTION

Figure 1:
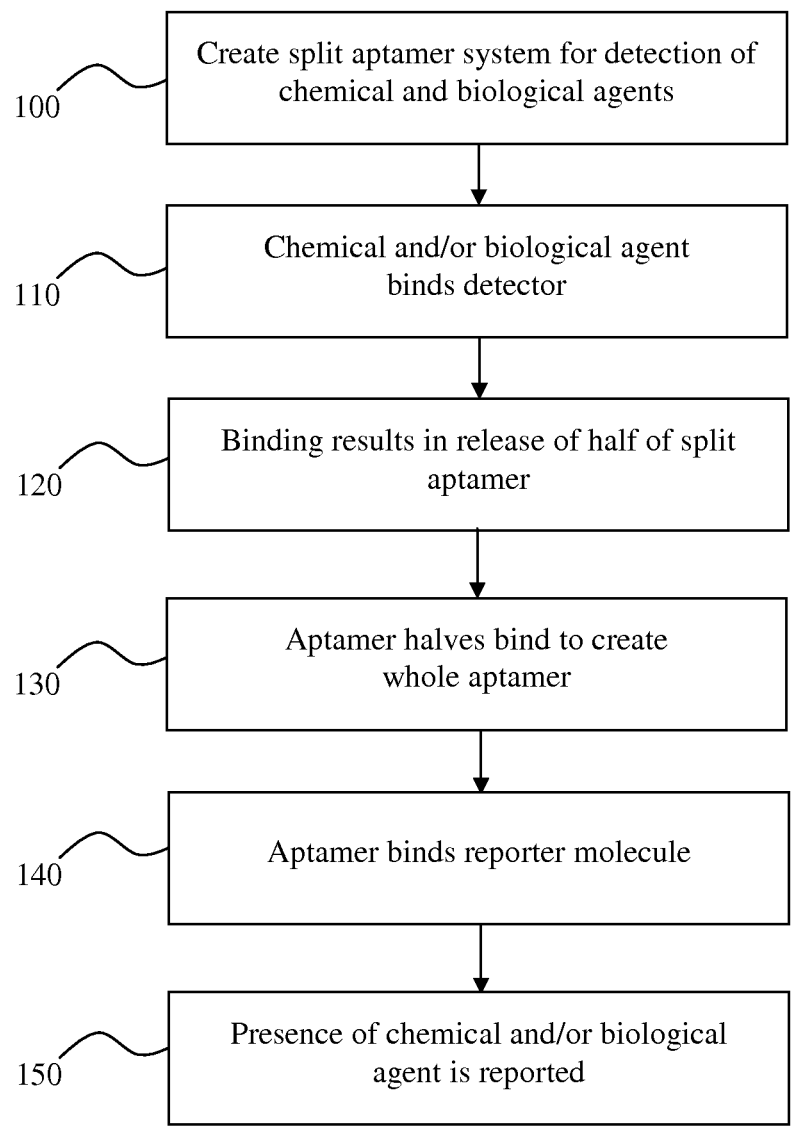
FIG. 1 is a flowchart of an exemplary process for detecting the presence of a chemical or biological agent using an aptamer in accordance with an embodiment of the present invention.

Referring now to the drawings wherein like reference numerals designate identical or corresponding parts or steps throughout the several views, there is shown in FIG. 1 a flowchart of an exemplary process for detecting the presence of a chemical or biological agent using aptamers. As an initial step 100, an aptamer with high specific affinity for a chemical or biological agent of interest is isolated, identified, or created. Examples of biological agents of interest which can be used as a biological weapon include numerous bacterium, virus, prion, and fungus varieties, as well as biological toxins. Examples of chemical agents of interest include mustard gas, chloride gas, and sarin, among many other examples.

The aptamer can be created using any of a number of known methods in the art for isolating, identifying, or creating aptamers. While some aptamers are known to occur in nature, there are several methods used to create aptamers with high specific affinity for a target ligand such as a chemical or biological agent. The SELEX (systematic evolution of ligands by exponential enrichment) method, for example, uses multiple rounds of in vitro selection to selective—and then selectively evolve—a suitable aptamer from a large library of randomly generated oligonucleotide sequences.

According to a preferred embodiment, the system employs a split aptamer system in which the two segments of the aptamer are blocked from interacting until ligand binds. Once a suitable aptamer is selected, it can be analyzed to determine how or where to split the aptamer into the two segments. Experimentation to design the aptamers will likely be required, although methods of designing suitable aptamers are known in the art. As an alternative to the above method, the aptamer can be created using a design process in which the aptamer is formed by the interaction of two halves.

Figure 2:
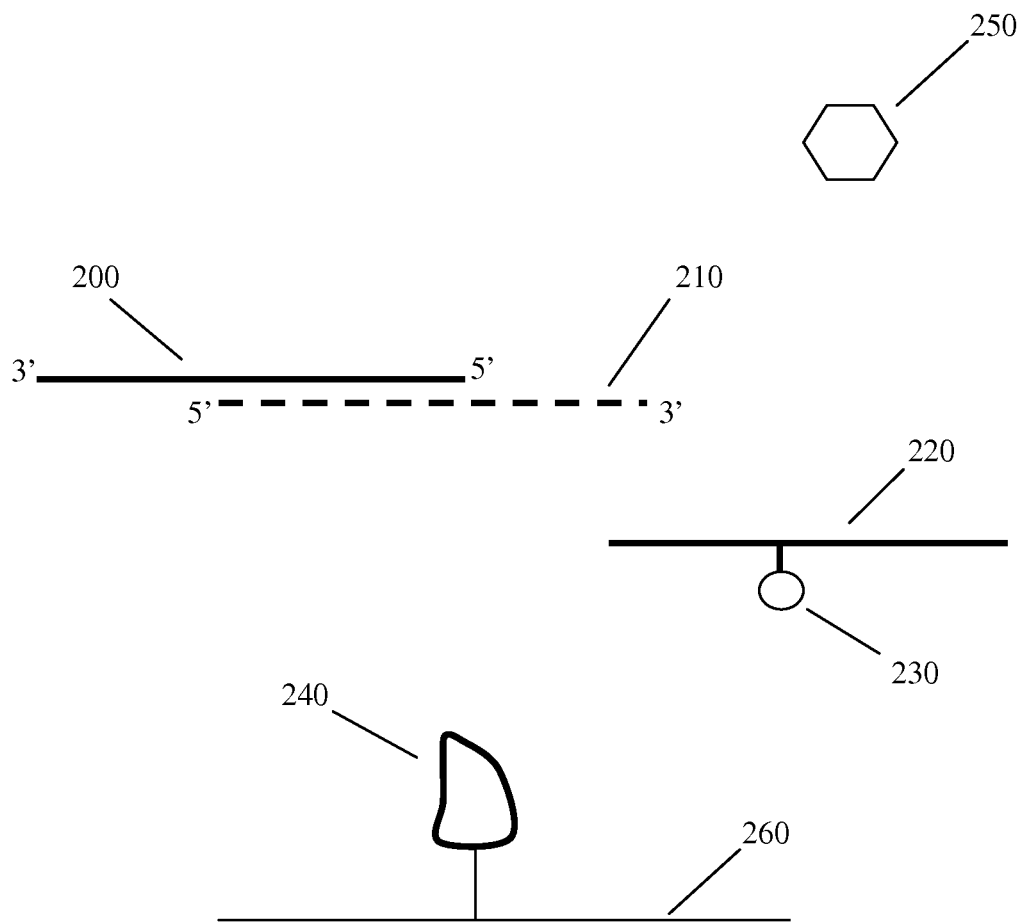
FIG. 2 is a schematic representation of a system for detecting the presence of a chemical or biological agent using an aptamer in accordance with an embodiment of the present invention.

FIG. 2 depicts a deployed split aptamer system in accordance with an embodiment of the present invention. The system comprises a first half of an anti-reporter oligonucleotide 200, an anti-biological or chemical agent aptamer 210, a second half of an anti-reporter oligonucleotide 220, a metal nanoparticle 230, a reporter molecule 240, a biological or chemical agent 250, and a conducting surface 260. In the absence of the target biological or chemical agent, the first half of the anti-reporter oligonucleotide 200 and the anti-biological or chemical agent aptamer 210 interact, preventing anti-reporter oligonucleotide 200 from interacting with anti-reporter oligonucleotide 220 to form a complete anti-reporter oligonucleotide.

Metal nanoparticle 230 can be any suitable metal or conductive compound, such as gold, platinum, or silver, among others. The metal nanoparticle can be bound to the anti-reporter oligonucleotide segment 220 using any one of a variety of methods known in the art, including but not limited to thiol binding. Similarly, conducting surface 260 can be any suitable conducting compound, and is preferably in communication with a detection circuit that is constantly or periodically monitoring one or more electrical characteristics of the system. Metal nanoparticle 230 and conducting surface 260 must be capable of an electrical interaction such that when they are in close proximity there is a change in the impedance and/or capacitance of the system, and the monitoring circuit can detect that change.

In other embodiments, the nanoparticle 230 is a redox reporter, an electrically-conducting or -insulating group, a chelating group (including but not limited to EDTA or ferrocene), or an electroconductive fluorophore. In each method, the nanoparticle, group, or molecule 230 is capable of being bound to the anti-reporter oligonucleotide segment 220 using any one of a variety of methods known in the art. The nanoparticle, group, or molecule 230 must be capable of reporting to the system under the prescribed circumstances or environment.

Figure 3:
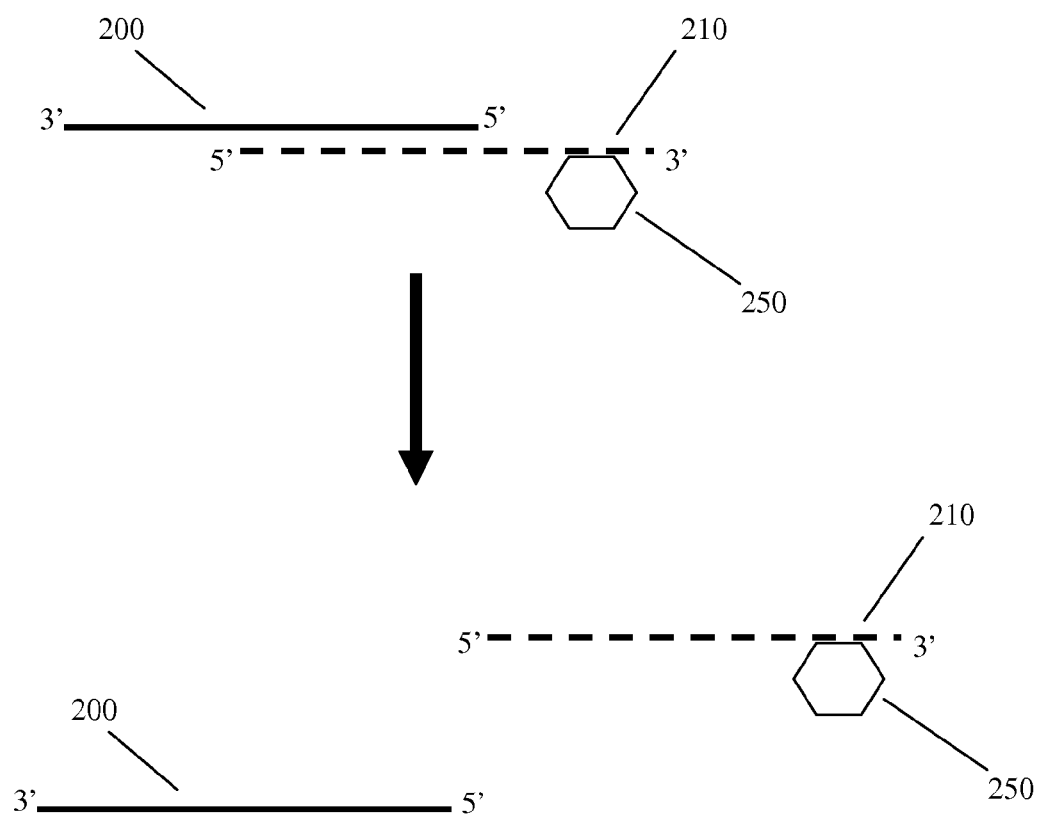
FIG. 3 is a schematic representation of a system for detecting the presence of a chemical or biological agent using an aptamer in accordance with an embodiment of the present invention.

At step 110 of the exemplary method depicted in FIG. 1, anti-biological or chemical agent aptamer 210 binds the target biological or chemical agent. Binding of the target biological or chemical agent causes a conformational change to the structure of the oligos at step 120 of the method, thereby releasing anti-reporter oligonucleotide 200, as shown in FIG. 3. Anti-reporter oligonucleotide 200 is then able to interact with anti-reporter oligonucleotide 220 to form a complete anti-reporter oligonucleotide 400, as stated in step 130 of the method and shown in FIG. 4.

At step 140, complete anti-reporter oligonucleotide 400 binds reporter molecule 240, thereby bringing metal nanoparticle 230 into close proximity to conducting surface 260, as shown in FIG. 5. When metal nanoparticle 230 is in close proximity to conducting surface 260, there is a change in the impedance and/or capacitance of the system. The change is detected by the system and reported at step 150, thereby alerting the system to the presence of the target chemical or biological agent.

FIG. 6 is a schematic representation of an array for detecting the presence of a chemical or biological agent using an aptamer in accordance with an embodiment of the present invention. The detection array 600 consists of multiple "spots" 610, or regions comprising one or more different types of aptamers against a chemical and/or biological agent. In one embodiment, each spot represents an aptamer recognizing a specific chemical or biological agent. The spot in column 4, row F may, for example, may contain aptamer that responds to the presence of anthrax spores, or any other chemical and/or biological agent.

Each spot of the array is preferably in communication with a circuit that detects the change in the impedance and/or capacitance of the system when a metal nanoparticle 230 is in close proximity to a conducting surface 260 within the spot. According to one embodiment, each different aptamer is represented within two or more spots on the array to avoid false positives and/or negatives. A logic circuit can be utilized to determine when to send a detection signal to the monitoring subsystem or station. For example, to minimize false positives, the logic circuit might require detection by at least two separate spots comprising aptamer directed to the same chemical and/or biological agent before it sends a detection signal to the monitoring subsystem or station.

Detection array 600 can be miniaturized such that it can be placed in numerous locations. Since each spot on the array can comprise at maximum a small number of aptamers, the spot can be extremely small. Detection array 600 can also be separate from, and/or remote from, the reporting center. In one embodiment, one or more spots within the detection array detects the target chemical and/or biological agent and the circuit on the array responds to that detection by sending a signal to a nearby signal receiver or transceiver. This signal can then be relayed by wired or wireless transmission to a reporting, tracking, or monitoring station or center. In one embodiment, the detection array detects a chemical and/or biological agent and sends the detection signal wirelessly to a local WiFi or cellular transceiver. The local WiFi or cellular transceiver then sends the detection signal to the reporting, tracking, or monitoring station or center. This remote detection and notification has the added benefit of detecting harmful chemical and/or biological agents in a standoff manner without requiring direct sampling.

There are a variety of other methods that can be used for the detection and reporting of a complete anti-reporter oligonucleotide 400. For example, other detection methods include Fluorescence resonance energy transfer ("FRET"), enzyme-substrate reactions including but not limited to ribozymes, surface plasmon resonance ("SPR"), quartz crystal microbalance, and luminescence, among many others. Each of these systems are well-known in the art.

Yet another possible mechanism for the detection and reporting of chemical and/or biological agents is surface plasmon resonance ("SPR"). Different anti-chemical and/or biological agent oligonucleotide is placed in wells of an SPR plate. Binding of the analyte to the oligonucleotide is detected and then reported by an SPR detector.

Although the present invention has been described in connection with a preferred embodiment, it should be understood that modifications, alterations, and additions can be made to the invention without departing from the scope of the invention as defined by the claims.

What is claimed is:

1. A sensor for detecting a target, comprising:
    a detection complex comprising: (i) an aptamer having a binding domain for said target, and (ii) a first oligonucleotide having a sequence complementary to a region of said aptamer, wherein in the absence of said target the aptamer and said complementary region of said first oligonucleotide form an intermediate combination, and wherein in the presence of said target the intermediate combination dissociates;
    a second oligonucleotide having a sequence that interacts with a region of said first oligonucleotide to form a duplex structure only when said first oligonucleotide is dissociated from said intermediate combination, wherein said second oligonucleotide comprises a metal nanoparticle, a redox reporter, an electrically-conducting or insulating group, a chelating group, or an electroconductive fluorophore; and
    a reporter molecule having a region that interacts with said duplex structure to form a reporter complex, wherein said reporter complex initiates a reporter signal.

2. The sensor of claim 1, wherein said target is a chemical or biological agent.

3. The sensor of claim 1, wherein said metal nanoparticle is selected from the group consisting of gold nanoparticle, silver nanoparticle, platinum nanoparticle, and combinations thereof.

4. The sensor of claim 1, wherein a reporter signal is generated when said metal nanoparticle is brought into close proximity with said reporter molecule.

5. The sensor of claim 1, wherein said sensor comprises an array of individual sensors for detecting a plurality of targets.

6. A sensor array for detecting a plurality of chemical and biological agents, comprising:
    a plurality of detection sensors, each of said plurality of detection sensors comprising:
        a detection complex comprising: (i) an aptamer having a binding domain for said chemical or biological agent, and (ii) a first oligonucleotide having a sequence complementary to a region of said aptamer, wherein in the absence of said target the aptamer and said complementary region of said first oligonucleotide form an intermediate combination, and wherein in the presence of said target the intermediate combination dissociates;
        a second oligonucleotide comprising a metal nanoparticle and having a sequence that interacts with a region of said first oligonucleotide to form a duplex structure only when said first oligonucleotide is dissociated from said intermediate combination; and
        a reporter molecule having a region that interacts with said duplex structure to form a reporter complex, wherein said reporter complex initiates a reporter signal.

7. The sensor array of claim 6, wherein said metal nanoparticle is selected from the group consisting of gold nanoparticle, silver nanoparticle, platinum nanoparticle, and combinations thereof.

8. The sensor array of claim 6, wherein a reporter signal is generated when said metal nanoparticle is brought into close proximity with said reporter molecule.

9. A method of detecting a target, the method comprising the steps of:
    contacting a sample with a sensor comprising a detection complex, said detection complex comprising: (i) an aptamer having a binding domain for said target, and (ii) a first oligonucleotide having a sequence complementary to a region of said aptamer, wherein in the absence of said target the aptamer and said complementary region of said first oligonucleotide form an intermediate combination, and wherein in the presence of said target the intermediate combination dissociates;
    forming a duplex structure between the dissociated first oligonucleotide and a second oligonucleotide, said second oligonucleotide comprising a metal nanoparticle, a redox reporter, an electrically-conducting or -insulating group, a chelating group, or an electroconductive fluorophone and having a sequence that interacts with a region of said first oligonucleotide only when said first oligonucleotide is dissociated from said intermediate combination;
    forming a reporter complex between said duplex structure and a reporter molecule; and
    generating a reporter signal by said reporter complex.

10. The method of claim 9, wherein said target is a chemical or biological agent.

11. The method of claim 9, wherein said second oligonucleotide further comprises a metal nanoparticle.

12. The method of claim 11, wherein said metal nanoparticle is selected from the group consisting of gold nanoparticle, silver nanoparticle, platinum nanoparticle, and combinations thereof.

13. The method of claim 11, wherein a reporter signal is generated when said metal nanoparticle is brought into close proximity with said reporter molecule.

14. The method of claim 9, wherein said sensor comprises an array of individual sensors for detecting a plurality of targets.

* * * * *